United States Patent [19]

Watanabe et al.

[11] Patent Number: 5,071,760

[45] Date of Patent: Dec. 10, 1991

[54] METHOD FOR CULTURING AND FLOATING ANIMAL CELLS IN A DOUBLE-BAG CONTAINER

[75] Inventors: Katsuto Watanabe, Hadano; Yoshihiko Nakamura, Isehara; Takashi Noto, Ayase; Masaichi Yamamura, Atsugi; Hitoshi Nakashima, Sagamihara; Kazunori Ichinohe, Sagamihara; Yukitaka Mino, Sagamihara; Kazuhiro Nishijima, Sagamihara, all of Japan

[73] Assignee: Kawasumi Laboratories Inc., Tokyo, Japan

[21] Appl. No.: 656,122

[22] Filed: Feb. 14, 1991

Related U.S. Application Data

[63] Continuation of Ser. No. 90,226, Aug. 27, 1987, abandoned.

[30] Foreign Application Priority Data

| Aug. 27, 1986 | [JP] | Japan | 61-198898 |
| Mar. 31, 1987 | [JP] | Japan | 62-46745[U] |
| Apr. 3, 1987 | [JP] | Japan | 62-80991 |
| Jul. 11, 1987 | [JP] | Japan | 62-172101 |

[51] Int. Cl.$^5$ ............................ C12N 5/06; C12N 5/02
[52] U.S. Cl. ............................ 435/240.25; 435/240.1; 435/240.241

[58] Field of Search ............... 435/2, 240.1, 240.22, 435/240.241, 240.25, 284–286, 311, 316, 182; 604/408, 410, 416, 903; 366/208, 209, 210, 214, 216, 217; 383/37, 40

[56] References Cited

U.S. PATENT DOCUMENTS

| 2,494,866 | 1/1950 | Fressola | 366/210 |
| 4,183,677 | 1/1980 | de Bruyne | 366/209 |
| 4,293,643 | 10/1981 | Ohtake et al. | 366/214 |
| 4,296,205 | 10/1981 | Verma | 435/240.241 |
| 4,661,455 | 4/1987 | Hubbard | 435/240.241 |

FOREIGN PATENT DOCUMENTS

| 3248543 | 7/1983 | Fed. Rep. of Germany | 435/240.25 |
| 1530705 | 11/1978 | United Kingdom . | |

Primary Examiner—David L. Lacey
Assistant Examiner—William H. Beisner
Attorney, Agent, or Firm—Michael J. Striker

[57] ABSTRACT

The instant invention relates to a method for culturing and floating animal cells in a double-bag container, where an outer bag containing culture media and a volume of air houses an inner bag of a semipermeable film containing cells suspended in a culture media. The semipermeable film has pores of sufficient size so as to prohibit cells within the inner bag from passing therethrough but allowing culture liquid and air to pass through it. To optimize the exchange of nutrients between the interiors of the two bags, a protective mesh surrounds the inner bag and the double-bag container is fastened to an agitator which provides either a rotating or shaking motion.

5 Claims, 12 Drawing Sheets

FIG_1
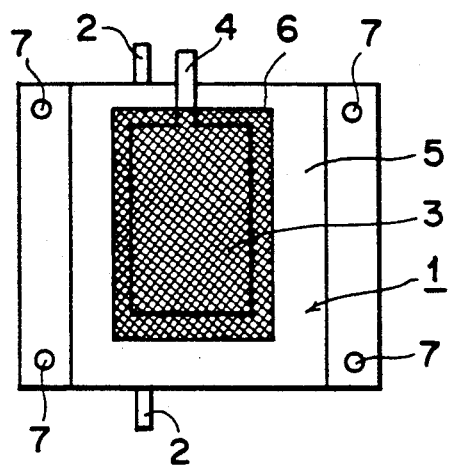
FIG_4
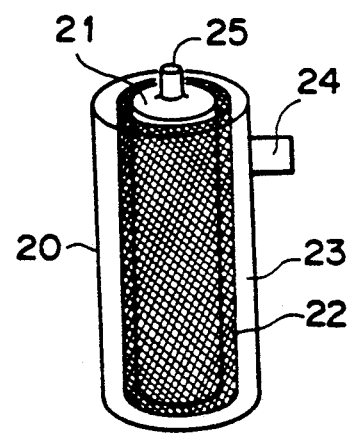
FIG_2
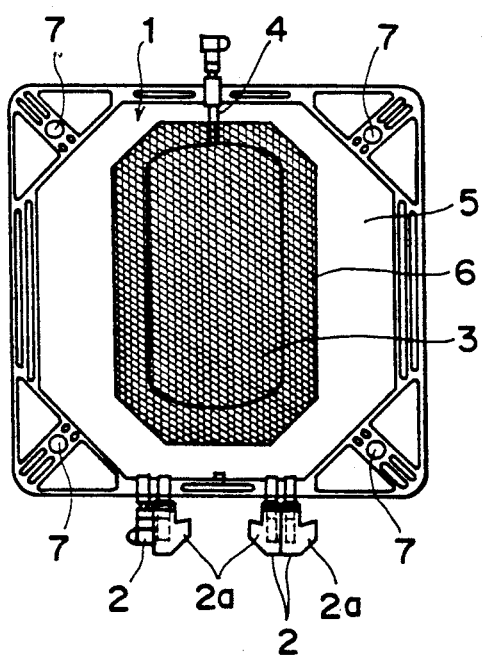
FIG_3(A)
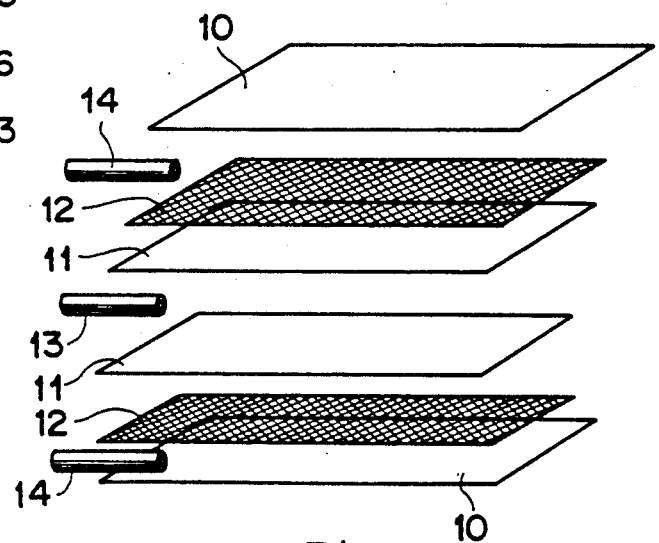
FIG_3(B)
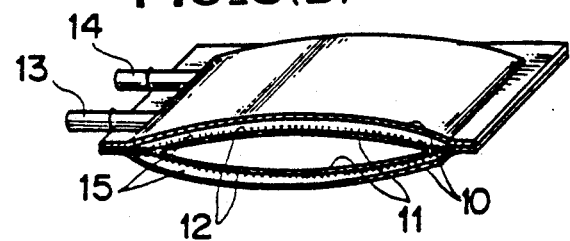

FIG._5(A)
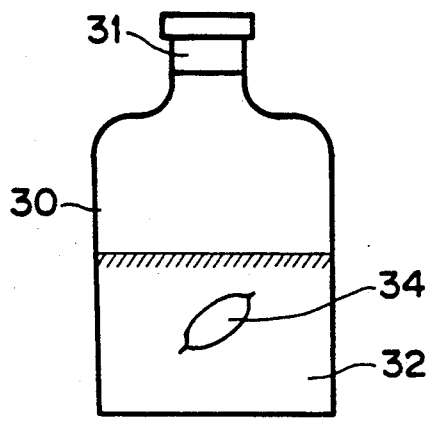
FIG._5(B)
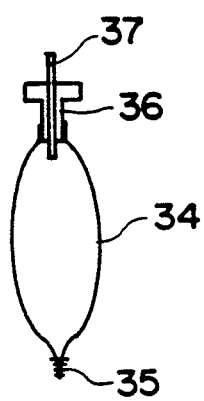
FIG._6
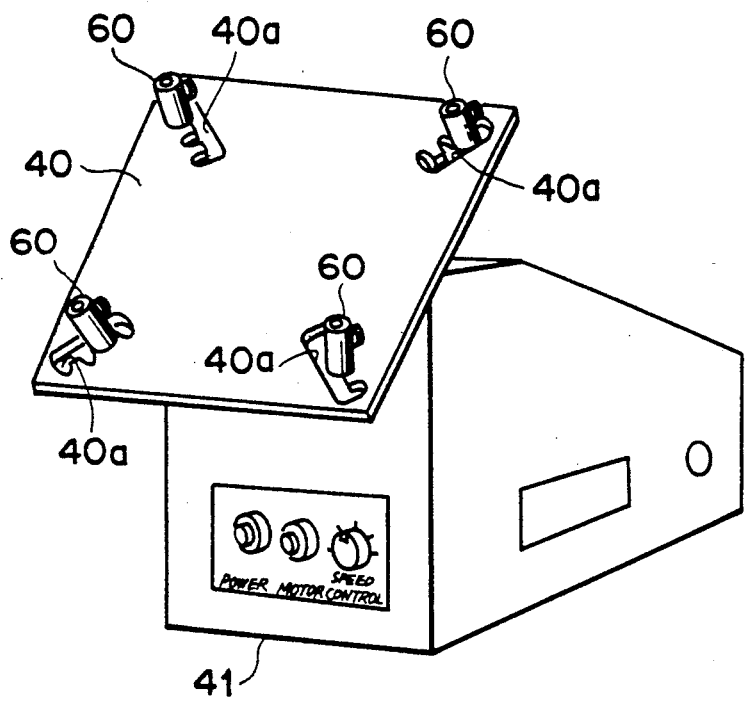
FIG._7
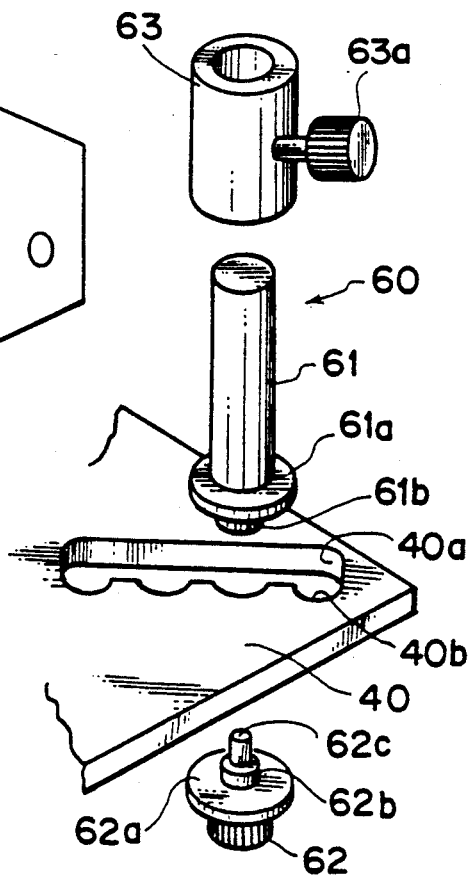

FIG_8
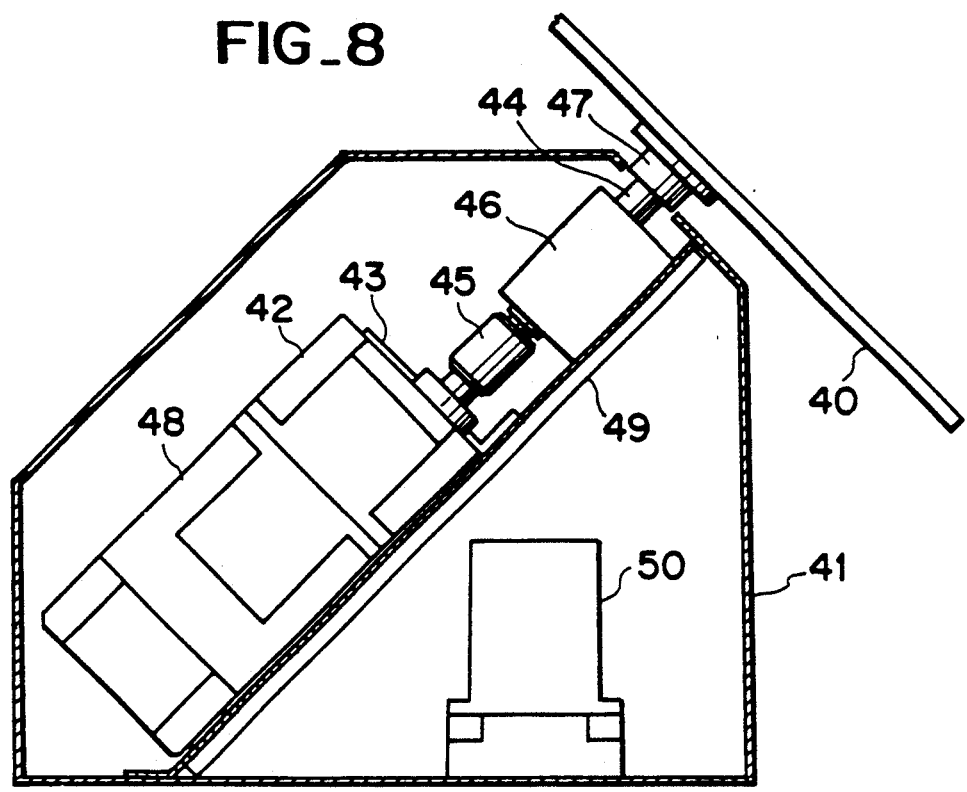
FIG_9
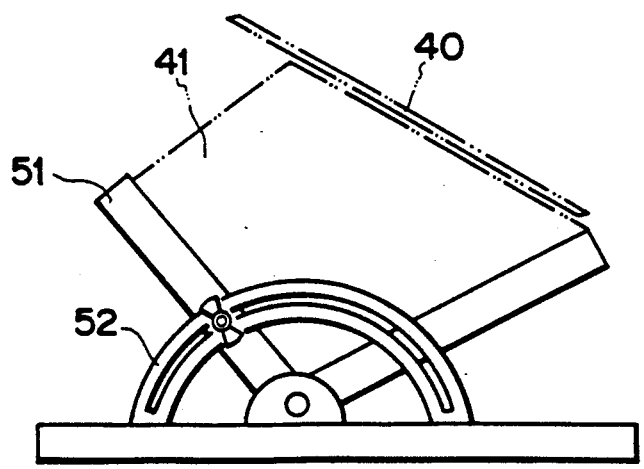

FIG._10
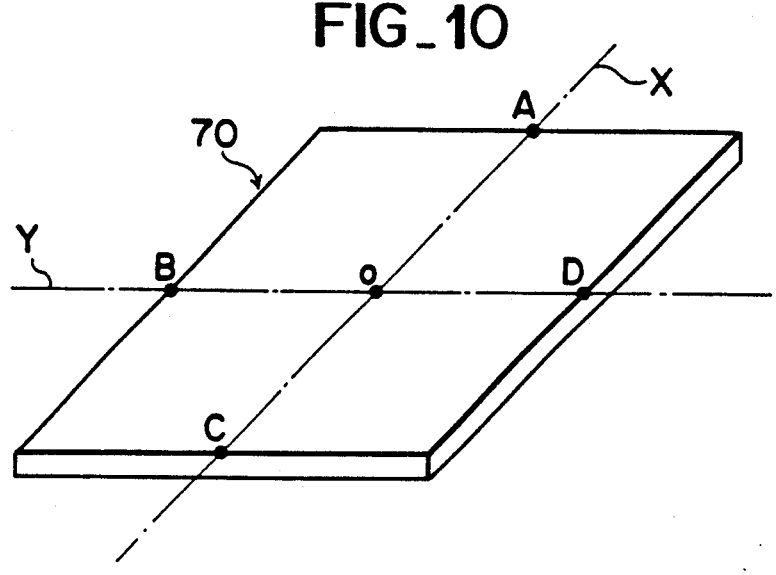
FIG._11
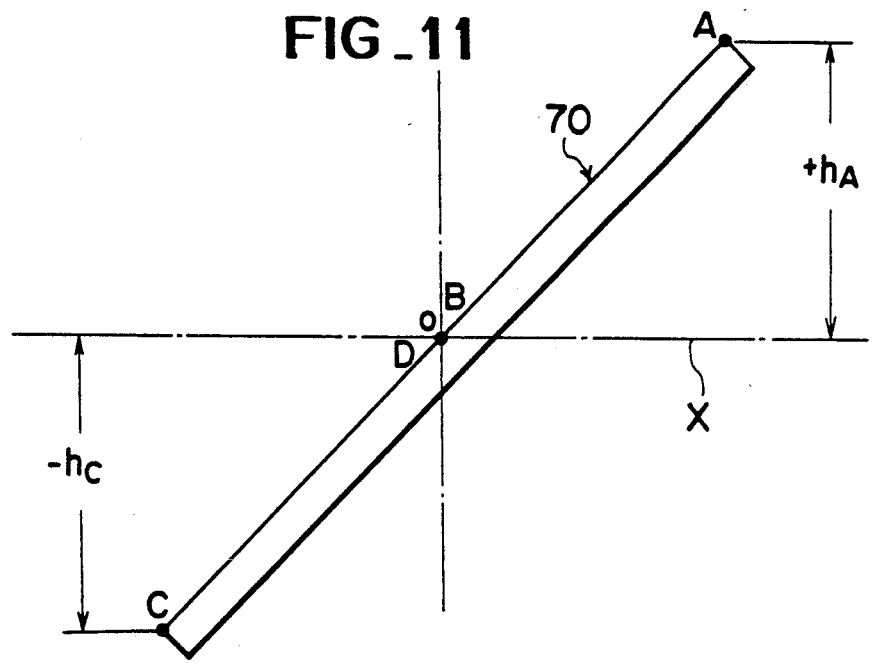
FIG._12
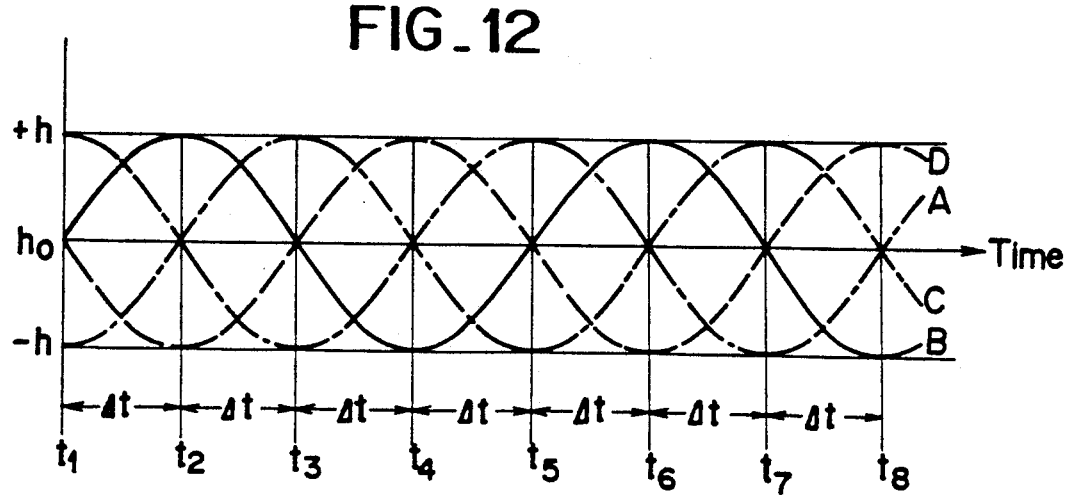

FIG_13
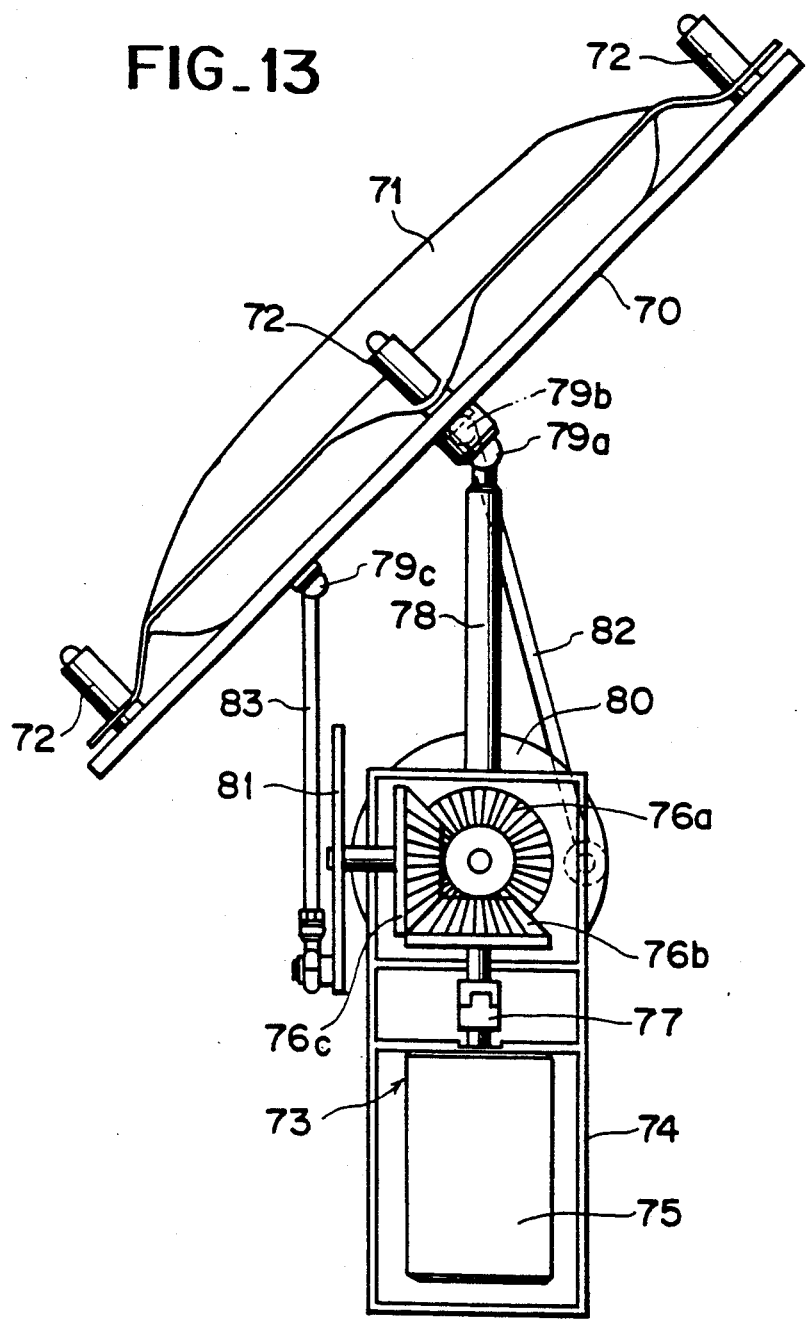
FIG_14
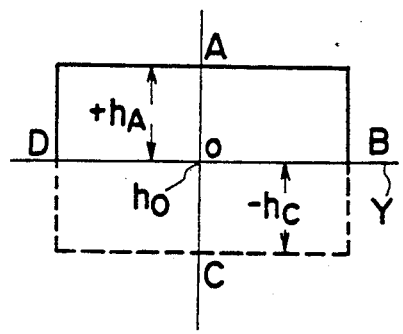
FIG_15
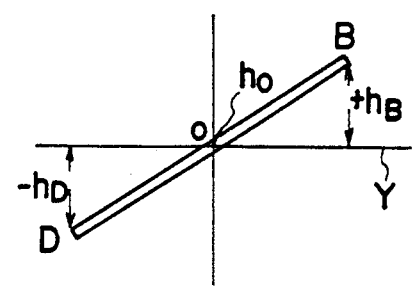

FIG_16
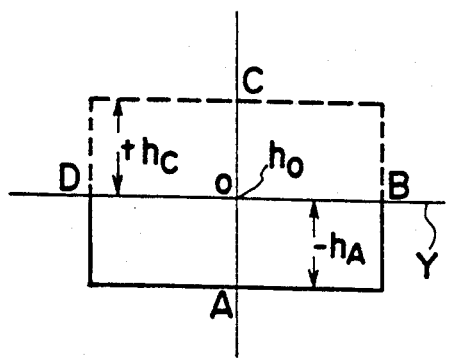
FIG_17
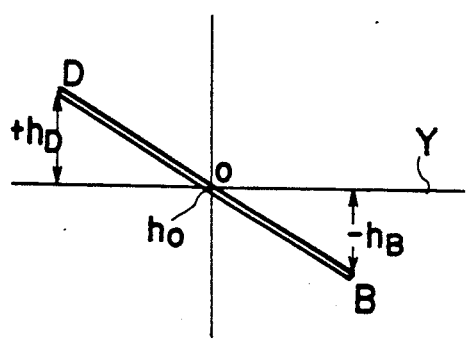
FIG_18(A)
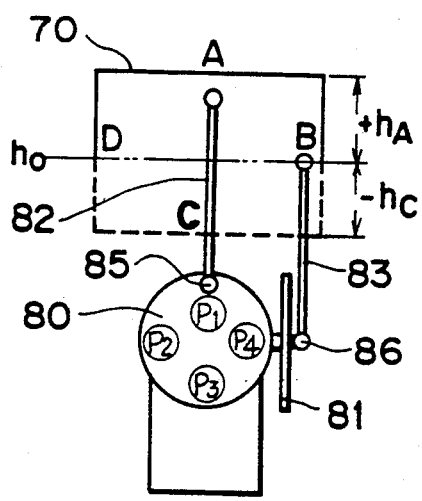
FIG_19(A)
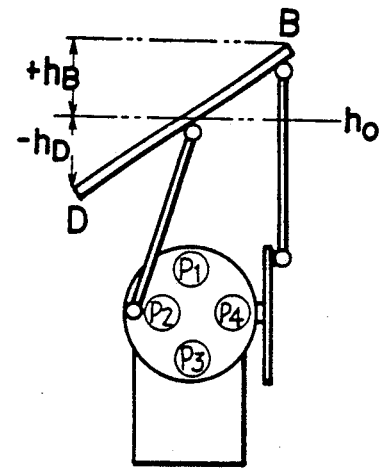
FIG_18(B)
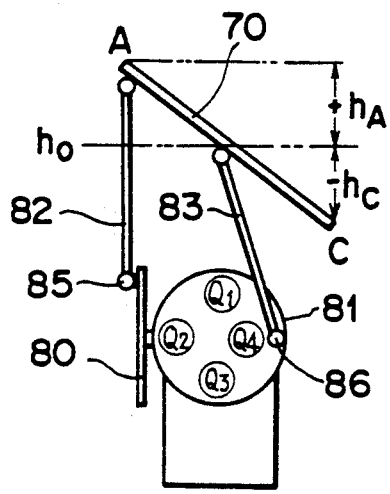
FIG_19(B)
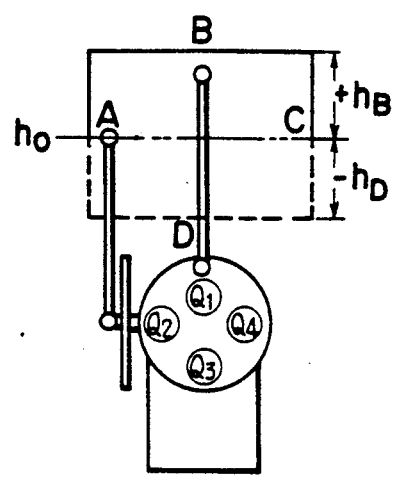

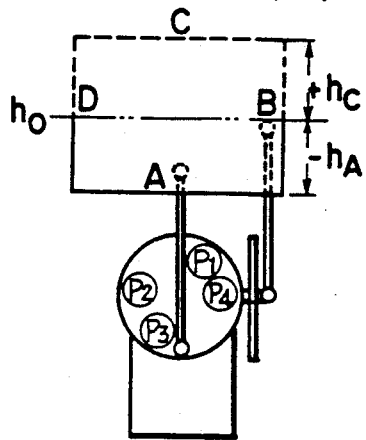
FIG_20(A)
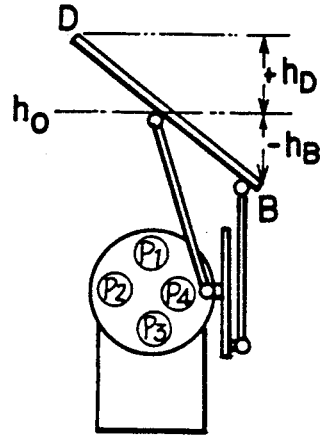
FIG_21(A)
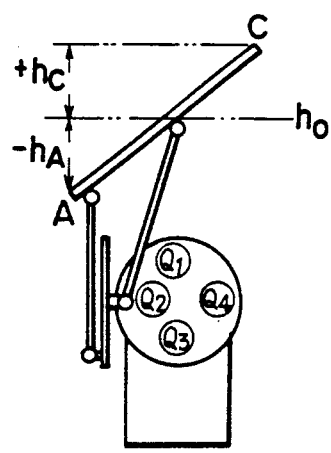
FIG_20(B)
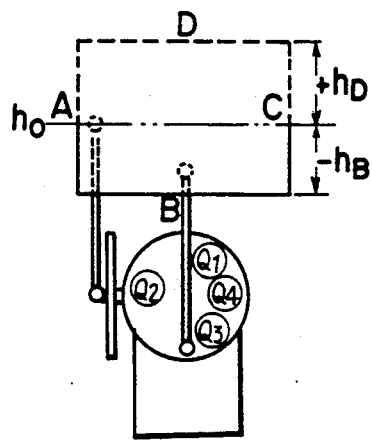
FIG_21(B)
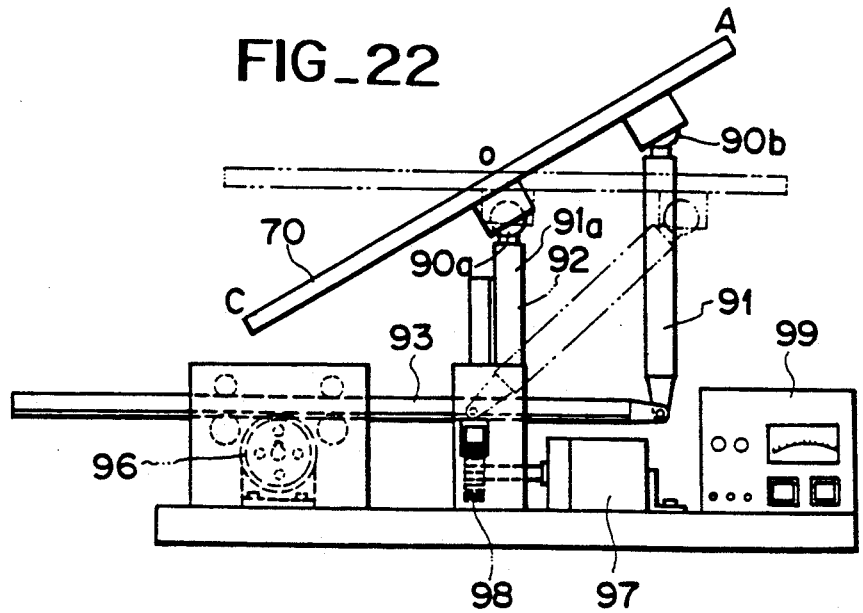
FIG_22

FIG_23
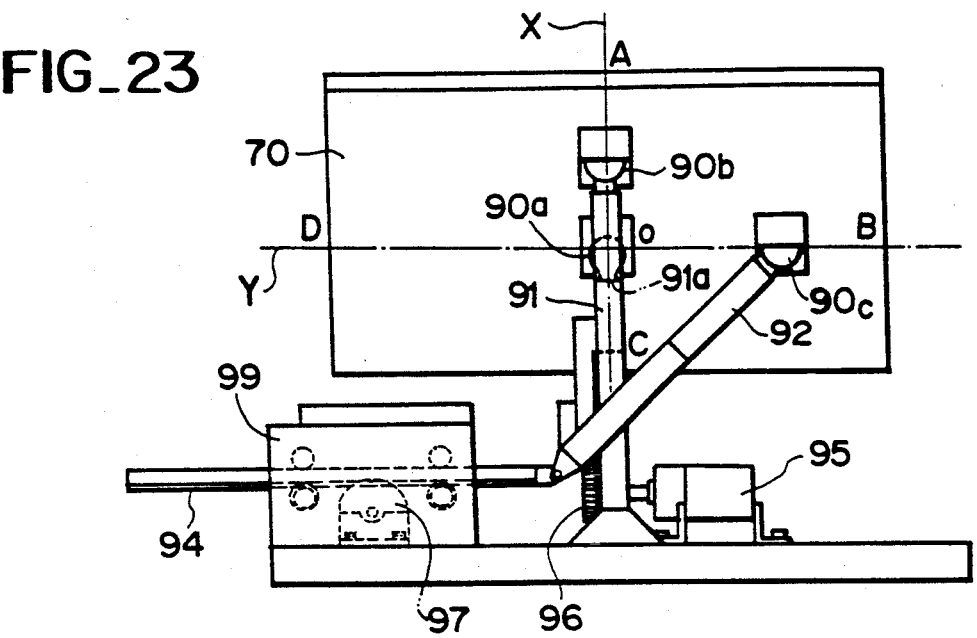
FIG_24
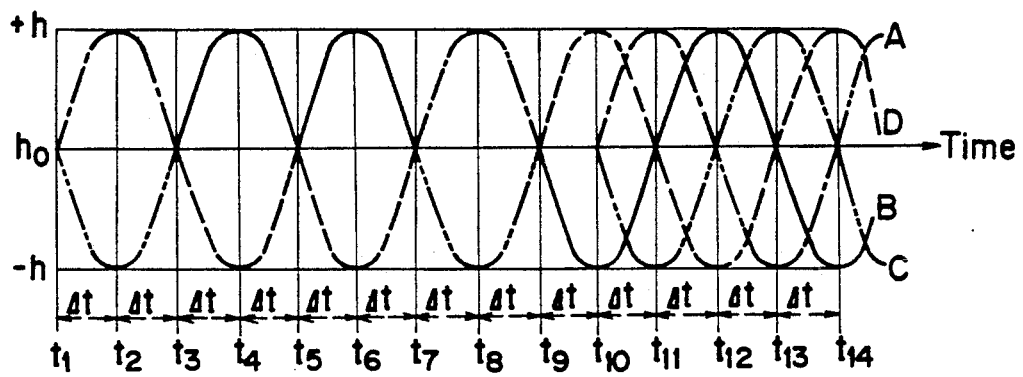
FIG_25
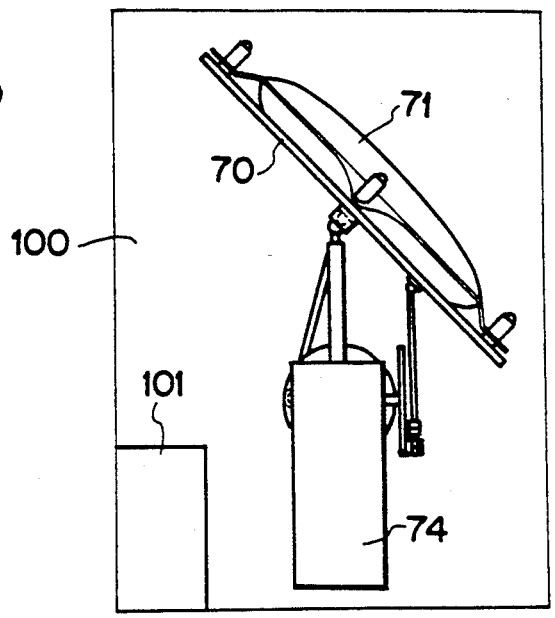

FIG._26
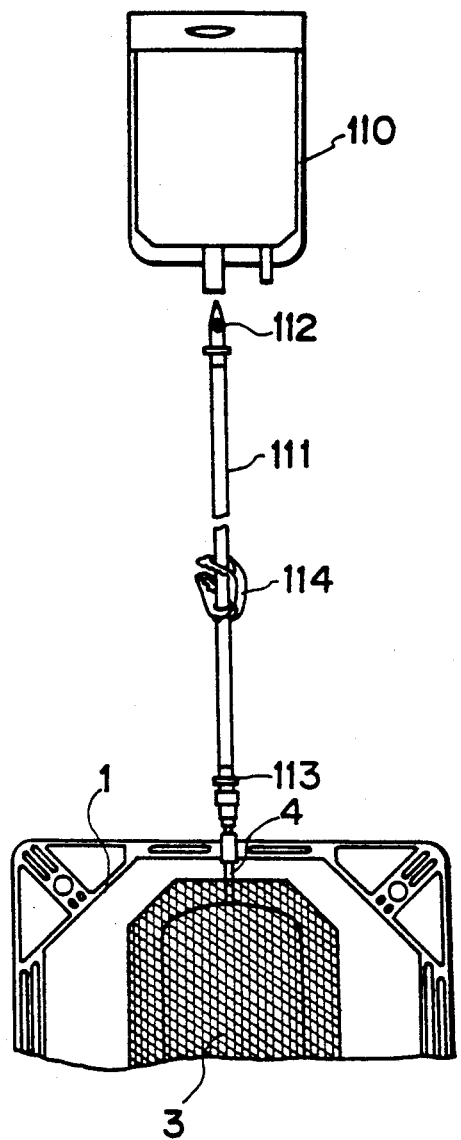
FIG._27
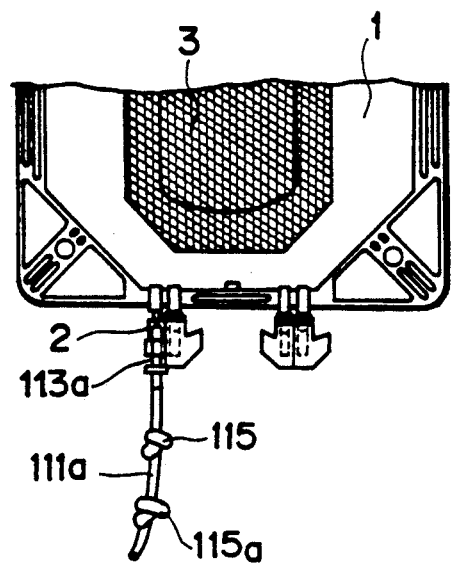
FIG._28
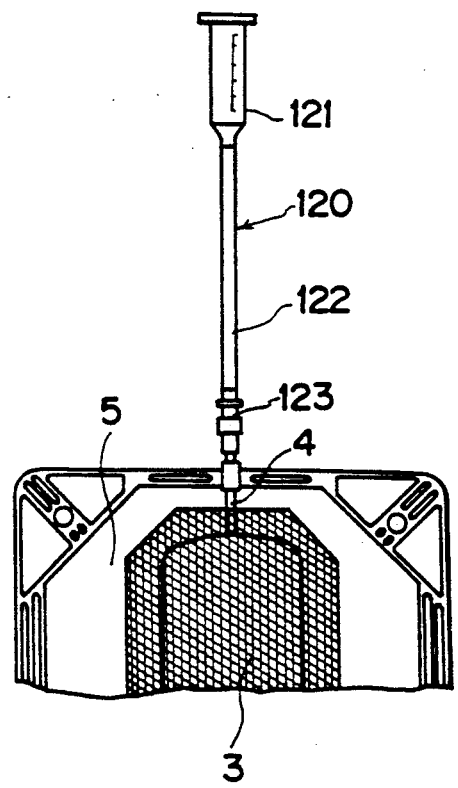
FIG._29
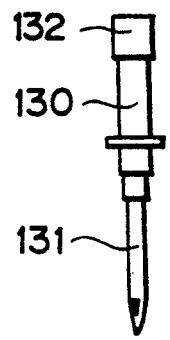

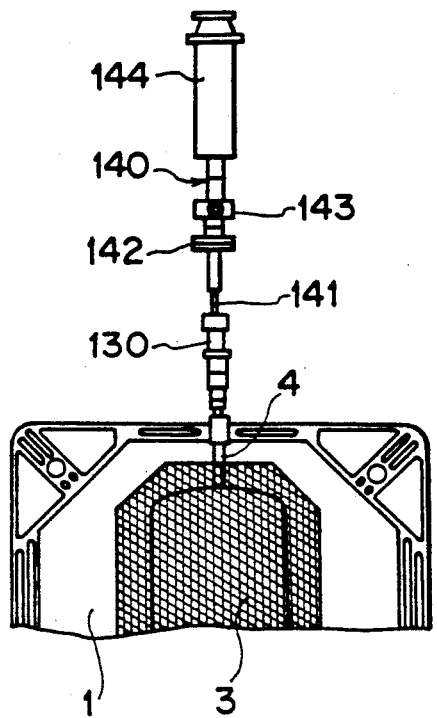
FIG_30
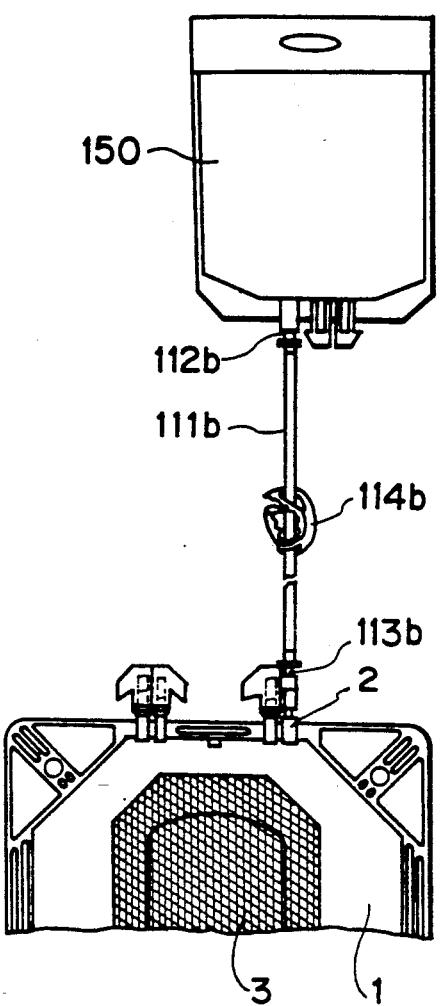
FIG_31
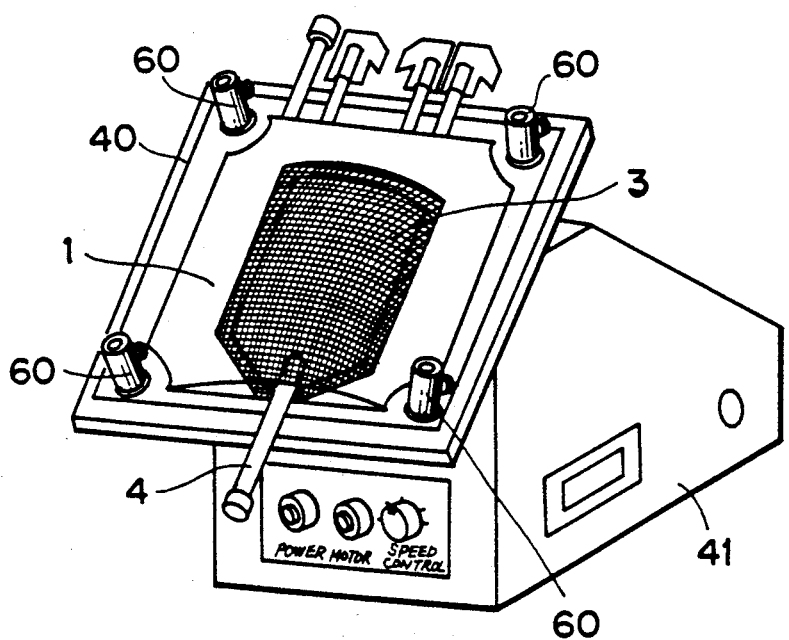
FIG_32

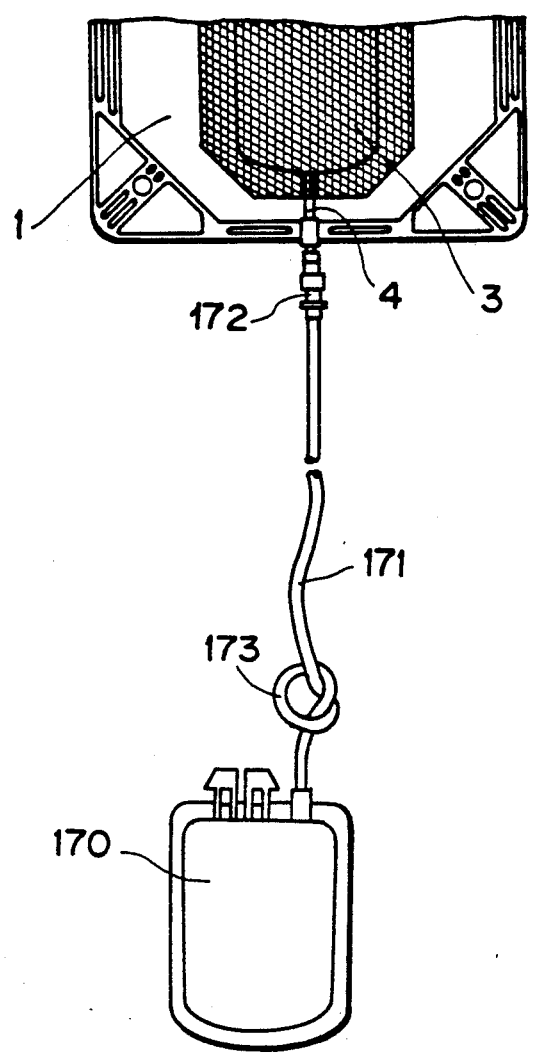
FIG_33
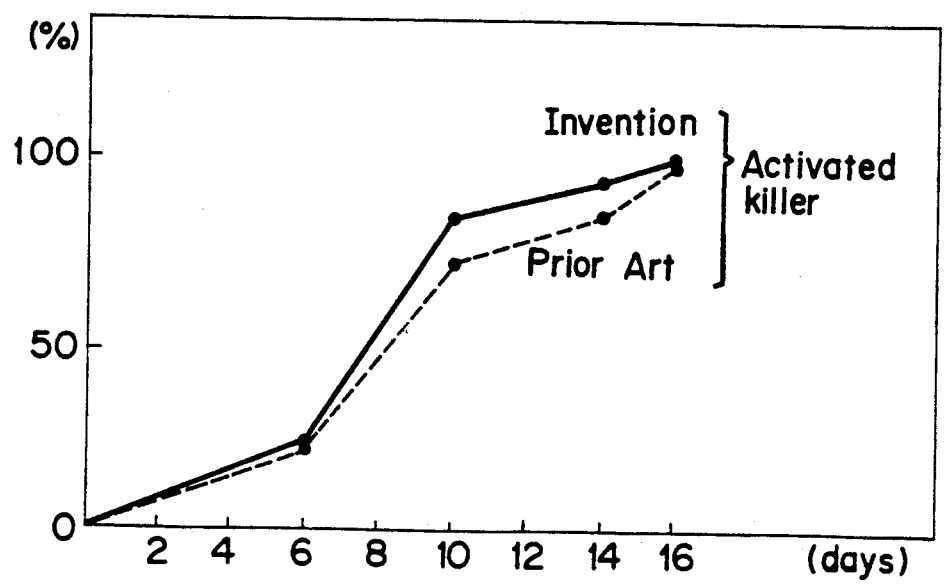
FIG_34

FIG_35
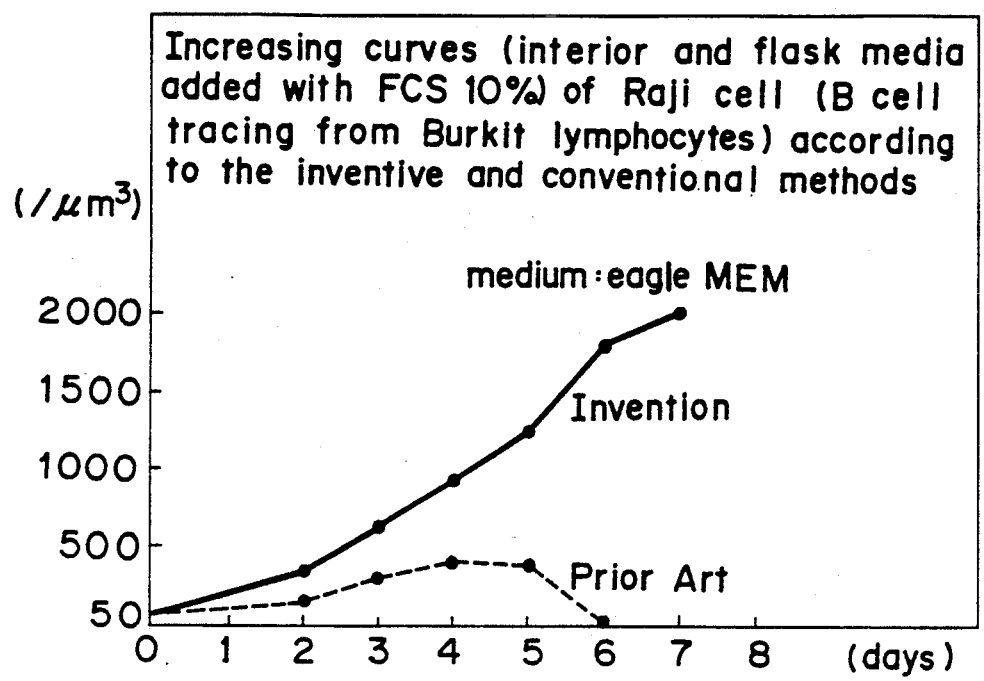
FIG_36
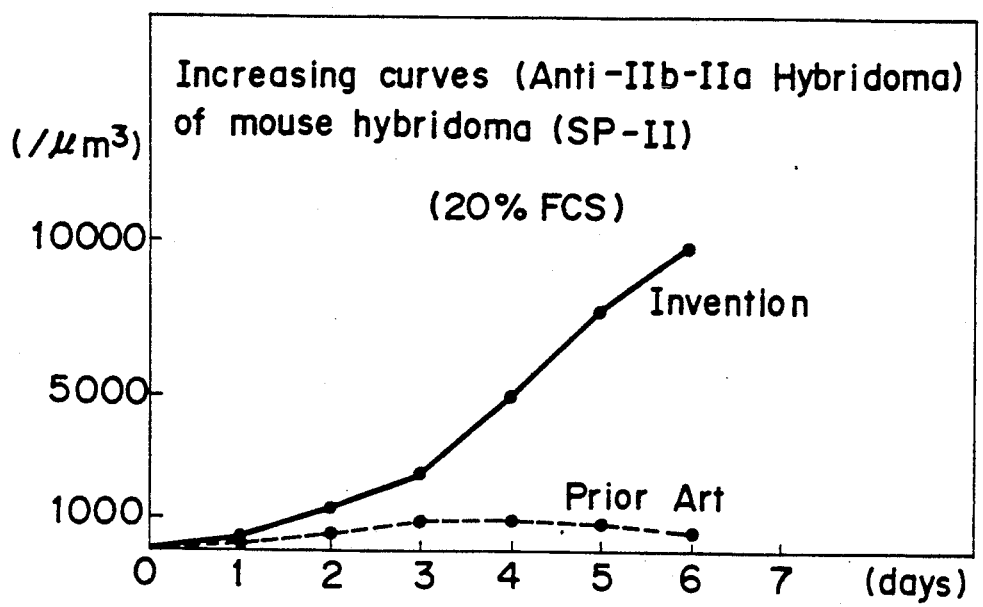

METHOD FOR CULTURING AND FLOATING ANIMAL CELLS IN A DOUBLE-BAG CONTAINER

This application is a continuation of application Ser. No. 090,226, filed Aug. 27, 1987, now abandoned.

BACKGROUND OF THE INVENTION

This invention relates to a method and an instrument for cultivating tissue cells at high concentration or high activity.

DESCRIPTION OF THE PRIOR ART

Known cultivating methods for animal tissue cells use flask cultivation in liquid media. For example, a rotary cell culture causes the cells to attach to the inner wall of a roller bottle or to float in the bottle; another method causes the cells to attach to the surfaces of beads and cultivate there; or a further method causes the cells to attach to a hollow membrane made of a semipermeable membrane film, and supplies a cultivating liquid to a rear side of the membrane.

However, with respect to those conventional methods, when culture media for the cells floating because of the roller bottle are exchanged, the cells are subsided or precipitated by means of for a centrifugal operation. This operation is not only troublesome but also dangerous in the possibility of pollution. Further, the methods using the rotary cell culture or the beads attaching are difficult in yielding the cells, and require a provision as a thermostatic chamber or an exclusive incubator. In a hollow fibre membrane or the semipermeable membrane film, since the cells attach thereto, the yielding is poor, and if a high density cultivation is required, the area of the hollow fiber or the film membrane should be broadened. In addition, an instrument is required for circulating the cultivating liquid and for supplying it, and as a whole the instrument will be of large size and high cost.

SUMMARY OF THE INVENTION

The present invention has been developed through many investigations to remove problems at issue in the prior art.

It is an object of the invention to provide a method for cultivating the tissue cells by an effective and economical way at high concentration or high activity.

It is another object of the invention to provide an instrument for practising the present cultivating method efficiently and economically.

For cultivating the tissue cells, the invention encloses the cells within a container of a semipermeable membrane film together with cultivating media and gas, and retains the media and the gas outside of the semipermeable membrane film, thereby to cultivate the cells through the semipermeable membrane film at high density by the media in the semipermeable membrane film container as well as by the diffusion phenomena by attendency of the media to concentrate outside of said film. It is preferable to cultivate the cells while rotating or turning the container at angles desirable for the cultivation of the cells.

A cultivating instrument is provided with a container of the semipermeable membrane film for holding an amount of a culture liquid with the cells to be cultivated and with another container for holding another amount of culture liquid and the gas in which the semipermeable membrane film container is immersed, and the communication between the former and latter containers is established via the semipermeable film membrane.

The semipermeable membrane film may be of cellulose such as regenerated cellulose or cellulose acetate, or a film such as polyacrylonitrile, polymethylmetacrylate, polysulfone, polycarbonate, polyamide, polyethylene, polypropylene, ethylenevinylalchole, chitin or chitosan.

Pore sizes depend upon the sizes of the cells or the cultivating liquid, but they are sufficient for passing the cultivating liquid and the gas, not passing the cells, when the pore size is preferably not more than $0.2\mu$. If additives are supplied other than the cultivating liquid, the pore sizes should be selected taking the sizes of the additives into consideration (when the additives are given within the semipermeable membrane film container, the pore size should be selected not to pass the additives, and when they are given to the cultivating liquid outside of the film, the pore size is selected to pass them but not to pass useful products obtained from the cells).

Preferably, a mesh-like cover encircles the semipermeable membrane film container, and the communication mouth may be plural, if required.

While cultivating the cells in the container, the container is rotated or shaked to slowly agitate the cells, so that the interior liquid and the exterior liquid are effectively contacted with each other through the semipermeable membrane film, and the cells are avoided from adhering to the inner wall thereof, and the yielding efficiency of the cells may be increased. The agitator comprises a fixing plate for supporting the cultivating container and a rotating or shaking mechanism of the fixing plate. The rotation system is not limited to specific angles, but could obtain desired results at angles of 30°, 45° or 60°.

BRIEF DESCRIPTION OF THE DRAWINGS

FIG. 1 shows an elevation view of a cultivating container of the present invention;

FIG. 2 shows a modification of the cultivating container;

FIG. 3(A) shows another embodiment of a cultivating container of the invention, in a dismantled configuration.

FIG. 3(B) shows the assembled container of FIG. 3(A) in half cross-section.

FIG. 4 shows a perspective view of another embodiment of the container of this invention;

FIG. 5(A) shows a further embodiment of an outline of an outer container.

FIG. 5(B) shows an outline of an inner container as shown in FIG. 5(A).

FIG. 6 shows a whole perspective view of a rotary cell cultivating device which will use the container of the invention;

FIG. 7 shows an exploded view showing a fixing means of the container in the device of FIG. 6;

FIG. 8 shows an outline for explaining a drive mechanism of the device of FIG. 6;

FIG. 9 shows a sectional side view showing a bed for mounting the rotary cell cultivating device;

FIG. 10 shows an explanatory view for actuating a shaking plate for cultivating the cells while shaking the container;

FIG. 11 shows a side view of the plate of FIG. 10;

FIG. 12 shows a graph showing the time changing between a center O and heights of points A, B, C, D of the plate of FIG. 11;

FIG. 13 shows an elevation view of the shaking device for moving the shaking plate at periods according to FIG. 12;

FIGS. 14 to 17 show outlines for explaining actuations of the shaking plate of FIG. 11 in accordance with the periods according to FIG. 12;

FIGS. 18(A), 19(A), 20(A) and 21(A) show outlines actuating changes of the shaking device in response to movements of the shaking plate of FIGS. 14 to 17, where the outlines depict a rear view of FIG. 13.

FIGS. 18(B), 19(B), 20(B) and 21(B) depict a right side view of FIGS. 18(A), 19(A), 20(A) and 21(A), respectively.

FIG. 22 show an outline of a shaking device for actuating the cultivating container at another period;

FIG. 23 show a right side view of FIG. 22;

FIG. 24 show a graph showing time changing between a center O and heights points A, B, C, D of the shaking plate actuated by the device of FIGS. 22 and 23;

FIG. 25 shows an outline showing cultivation while controlling temperature when the shaking cultivation device is positioned in a sealed chamber;

FIGS. 26 to 33 show outlines for explaining sequences of operating the cultivating instrument of the invention;

FIG. 26 shows an outline for explaining washing of the cultivating container;

FIG. 27 shows an outline of sealing a communicating tube after an outer bag has been washed;

FIG. 28 shows an outline of a connection of a charging instrument for charging the floating cells into an inner bag;

FIG. 29 shows an adapter to be used in this invention;

FIG. 30 shows an outline showing a connection of the inner bag to a sterilized air charging instrument;

FIG. 31 shows an outline of a connection of an outer bag to a culturing bag;

FIG. 32 shows a perspective view showing the container attached to the shaking cultivation device;

FIG. 33 shows an outline of a connection of a cell yield bag to the inner bag;

FIG. 34 shows a graph showing activated killer LAK cells obtained by the inventive and conventional methods;

FIG. 35 shows a graph showing increasing curves of Raji cells; and,

FIG. 36 shows a graph showing increasing curves of mouse hybridoma.

DETAILED DESCRIPTION OF PREFERRED EMBODIMENTS OF THE INVENTION

FIG. 1 is an elevation view showing an example of the cultivating container of the invention. A sealing bag 1 is made of soft or half hard plastic treated with single layer or laminate of vinyl chloride, ethylene acetate vinyl copolymer, polypropylene, polyethylene, polyester, Teflon or polyamid and communication mouths 2 are provided for charging the cultivating liquid and the gas at upper and lower parts. A mouth once used is sealed not to allow re-use.

Within the outer bag 1, semipermeable membrane film bag 3 is provided, and a space 5 outside of the bag 3 serves for holding the cultivating liquid. A communication mouth 4 is projected from the upper part of the outer bag 1 for charging the cells into the bag 3. The semipermeable membrane film bag 3 is encircled with a protecting mesh cover 6.

The outer bag 1 is composed by sealing two sheets of plastic at their peripheries. Plastic tubes acting as the communication openings or mouths 2, 4, are secured to the bag 1 so as to project through the seal at the upper and lower ends thereof, which tubes may be equipped with mouths (corresponding to a blood transfusion mouth for be used to a blood bag). The protecting mesh cover 6 is formed in the bag 1 and holds the semipermeable membrane film bag 3 therewithin.

The plastic sheet bag 1 is formed with holes 7 at four corners for securing the bag to a support when rotation or shaking is effectuated.

FIG. 2 shows a modification of the cultivating container of FIG. 1, and the same reference numerals are given to the same parts. A difference from FIG. 1 is that a plurality of mouths 2, 2 communicate with the interior of the outer bag 1 at the lower part of the bag 1. The communication mouths 2, 2 are sealed with protectors 2a.

FIG. 3(B) shows another example of the cultivating container which is assembled by holding two sheets 11, 11 of semipermeable film and two sheets 12, 12 of the outer mesh protecting cover between the outer plastic sheets 10, 10, and positioning the communication mouths 13, 14 between the sheets 11, 11 and between the outer sheets 10, 10 and the protecting cover sheets 12, 12 and melting the peripheries of the sheet assembly. Thus, the semipermeable membrane film bag is enclosed within the outer bag formed from the sheets 10, 10, and a space 15 between the inner and outer bags serves for containing the culture liquid and the gas outside of the inner bag.

FIG. 4 shows a further embodiment of the invention, where an outer sealing case 20 is cylindrical, and a tube made of a semipermeable membrane film 21 sealed at the lower end is housed therewithin, and a mesh-like protecting cover 22 encloses the outer part of the film tube 21.

Between the case 20 and the film tube 21, a culture media and gas container 23 is formed, and a communication mouth 24 is provided at a side of the sealing case 20 for communicating with the container 23, and a communication mouth 25 is provided at the upper part of the case 20 for communicating with the interior of the film tube 21.

FIG. 5(A) shows an instrument for easily reducing this inventive method to practice. The cells and the media are enclosed in bag 34 floating in cultivating liquid 32 in container 30 in the form of a glass or plastic bottle. The mouth of the container 30 is sealed with a plug 31. The bag 34 is, as shown in FIG. 5(B), sealed at its lower part 35 while its open upper part, shaped as a tube, is equipped with a rubber plug 36 to which a charging mouth 37 is connected.

FIG. 6 is a perspective view showing one example of a rotary cell cultivating device (agitator) to be used for agitation of the floating cells and media. The numeral 40 denotes a rotary plate, and 41 denotes a box where a rotation drive mechanism for the rotary plate 40 is housed.

The rotary plate 40 is inclined with respect to the horizontal surface, and is furnished with securing means or units 60 for holding the cultivating bag at four corners thereof. In the present embodiment, the angle of inclination of the plate 40 is 45°.

FIG. 7 shows a bag securing unit 60 in detail.

The rotary plate 40 is formed at its four corners, with holes 40a each extending toward the center of the rotary plate 40. Each hole 40a is formed with a plurality of arc shaped cutouts 40b for holding the securing unit 60 at several different positions.

The bag securing unit 60 is inserted into the hole 40 from the upper side of the rotary plate 40, and a securing screw 62 tightens it to the lower side of the rotary plate 40. A flange 61a is positioned about a lower portion of the pin 61, and a pin end portion 61b below the flange 61a has a diameter to be fitted into a cutout 40b of the pin holding hole 40a and is formed with a threaded hole (not shown).

The securing screw 62 is also formed with a flange 62a, and a stepped-down flange portion 62b formed at an end of the screw 62 has a diameter to be fitted into the cutout 40b of the hole 40a. The screw 62c is screwed into the threaded hole of the lower pin end portion 61b.

The flanges 61a, 62a engage from opposite sides the circumference of the hole 40a so as to secure the pin 61 to the rotary plate 40.

When the position of the pin 61 is to be adjusted, the screw 62 is loosened and the pin 61 is moved in the hole 40a, and the lower pin end portion 61b is moved into one of the cutouts 40b and the pin 61 is again secured to the rotary plate 40 by tightening the screw 62.

A cylindrical stopper ring 64 having a tightening screw 63a is slidably mounted on the pin 61, and if the screw 63a is tightened, the stopper ring 63 may be positioned at any level along the pin 61.

FIG. 8 is sectional side view showing a rotating drive mechanism of the rotary plate 40. Within the box 41, there is secured a plate 49 for supporting the drive parts, inclining at an angle (45° in this embodiment). The plate 49 supports a motor 48, a speed reduction gear head 42 and a bearing 46. The numeral 43 denotes a plate for supporting the motor 48.

A shaft is connected by a joint 45 between the gear head 42 and the bearing 46. A rotary output shaft 44 is supported by the bearing 46 and is fixedly connected at its with a part 47 for carrying the rotary plate 40 secured thereto by bolts.

A motor control unit 50 with a mechanism for controlling rotation of the motor 48 at determined speed is enclosed in the box 41 below the supporting plate 49. In this embodiment, the rotation speed of the rotary plate 40 may be determined within 0.5 to 10 rpm.

The structure of the securing means or units 60 for holding the cultivating bag of this invention and the rotation mechanism of the rotary plate 40 are not limited to the shown ones, but may be varied in response to demands.

As shown in FIG. 9, the rotary cell cultivating device is carried on an instrument 51 which is adjustable so as to control the angle of inclination of the entire device 41. The agitator rotates the cultivating device 41, but may turn it laterally and longitudinaly.

FIGS. 10 and 11 explain the shaking operation.

The numeral 70 designates a shaking plate for holding the cell cultivating device, where the point O is a center of the shaking plate, A and C are points on X-axis, running through the center point O, and B and D are points on Y-axis, running through the point O. The shaking plate 70 moves the cultivating device around the X and Y axes laterally and longitudinally.

FIG. 11 is a side view of the plate 70, showing a condition at which the plate 70 is moved around the Y-axis. Points A and C of the plate 70 are moved vertically in opposite directions in reference to zero height hO at the level of the center point O. A maximum range of turning of the points A and C is expressed with heights +hA, −hA and +hC, −hC (where "+" is the maximum value in a direction higher than hO, and "−" is the maximum value in a direction lower than hO). When moving the plate 70 around the X-axis, the moving range of points B and D is expressed by heights +hB, −hB, and +hD, −hD.

With respect to a first embodiment of the turning system for shaking plate 70, while the plate 70 turns around the X-axis (actually, the X-axis moves slightly in circle), the plate 70 turns simultaneously around the Y-axis (actually, the Y-axis also slightly moves in a circle).

A reference will be made to a case when the vertical and simultaneous turning movements of the plate 70 around the X- and Y-axes are repeated periodically. The cycles of h0 and hA, hB, hC, hD will be expressed with a formula (1).

$$\left.\begin{array}{ll} 1 & hA = \cos\omega t \\ 2 & hB = \cos(\omega t - \pi/2) \\ 3 & hC = \cos(\omega t - \pi) \\ 4 & hD = \cos(\omega t - 3/2\pi) \\ 5 & h0 = 0 \end{array}\right\} \quad (1)$$

Herein, h is height, t is time, and $\omega$ is angular velocity. The angular velocity is expressed with a following formula.

$$\omega = 2\pi f$$

(f is frequency).

At this time, the positioning relationship of ho and hA, hB, hC, hD are changed periodically as shown in a formula (2).

$$\left.\begin{array}{ll} 6 & hA > h0, hC < h0, hB = h0, hD = h0 \\ 7 & hA = h0, hC = h0, hB > h0, hD < h0 \\ 8 & hA < h0, hC > h0, hB = h0, hD = h0 \\ 9 & hA = h0, hC = h0, hB < h0, hD > h0 \end{array}\right\} \quad (2)$$

6, 7, 8, 9 of the formula correspond to t1, t2, t3, t4 of FIG. 12.

FIG. 12 shows periodical changes of hA, hB, hC, hD in time. It is seen that the vertical movements of points A, B, C, D of the plate 70 are in the relations having phases. The vertical turning movement of the plate 70, which will be explained with reference to the movement of point B of FIG. 12, means that the height hB of the point B periodically changes in one cycle between values h0→+hB→h0→−hB→h0.

FIGS. 14 to 17 show movements of the shaking plate 70 following this shaking cycle.

(a) As shown in FIG. 14, while the point A has the maximum height of +hA, and the point C has the maximum height of −hC relative to the X-axes, the points B and D are at the same zero height h0 relative to the Y-axis (t1 time in FIG. 12).

The plate 70 begins to turn around the Y-axis and the points A, C start to move towards the same zero height h0, and at the same time point B starts to move towards +hB about the X-axis, and point D starts to move towards −hD (t1+Δt time in FIG. 12).

(b) Subsequently, as shown in FIG. 15, point B is at the maximum height +hB, and point D is at the minimum height of −hD, and A and C are at the point same zero height h0 (t2 time in FIG. 12).

The turning plate 70 starts to turn about the X-axis, and points B, D move towards the same zero height of h0, and concurrently point A to −hA, and point C to −hC (t2+Δt time in FIG. 12).

(c) As shown in FIG. 16, the point C comes to the maximum height of +hC, the point A to −hA, and points B, D to the same zero height of h0 (t3 time).

The plate 70 starts to turn about the Y-axis, and gradually the points A, C come to the zero height of h0, point D to +hD, and point B to −hB.

(d) As shown in FIG. 17, the point D reaches the maximum height of +hD, and points A, C reach h0 (t4 time).

Thereafter, points B, D reach h0, the point A reaches +hA, and point C to −hC (t4+Δt time), and again they return to the (a) condition and repeat the (a) to (d) conditions.

TURNING SYSTEM I

FIG. 13 shows one example of a device for moving the shaking plate carrying the cell culture container in accordance with the above mentioned turning system I. A securing means for aculture container 71 is the same as that of FIG. 7. The center O of a shaking plate 70 is pivoted at a spatial angle by means of the link ball 79a arranged at an end of a pole 78 held by a box 74. Shaking plate 70 is driven by a drive mechansim 73. The box 74 encloses a motor 75 and gears 76a, 76b, 76c. These gears are in mesh with each other, and the gear 76b is connected to the motor 75 via a joint 77. The gear 76a is fixed with a link 80, and the gear 76c is fixed with a link 81. The link 80 is pivotably connected with one end of the push bar 82, and the other end of the bar 82 is pivotably connected with the plate 70 via the link ball 79b located on the X-axis (or Y-axis). Similarly, the link 81 is pivotably connected with one end of the push bar 83, and the other end of bar 83 is pivotably connected with the plate 70 via the link ball 79c, located on the Y-axis (or X-axis).

Actuation of the shaking device shown in FIG. 13 will be explained in comparison with the shaking movement of plate 70 shown in FIGS. 18(A), 18(B), 19(A), 19(B), 20(A), 20(B), 21(A), and 21(B).

Positions of the shaking device in FIGS. 18(A), 18(B), 19(A), 19(B), 20(A), 20(B), 21(A) and 21(B) correspond to those of FIGS. 14 to 17, where FIGS. 18(A), 19(A), 20(A), and 21(A) illustrate the outlines of the rear side of the device of FIG. 13, and FIGS. 18(B), 19(B), 20(B), and 21(B) illustrate the right side views of the device of FIG. 13.

(a') A connection 85 between the link 80 and the push bar 82 is at the position (P1), so that the push bar 82 moves the point A of the plate 70 upward to +hA, and the point C is moved down to −hC. At this time, since a connection 86 (pivot portion) between the link 81 and the push bar 83 is at the position (Q4), the points B, D of the plate 70 are at the same position as the center O (FIG. 18(A)).

(b') When the links 80, 81 turn 45° counterclockwise, the connection 85 between the link 80 and the push bar 83 moves to the position (P2), and the points A, C of the plate 70 are at the same height as the point O.

Since the connection 86 is at the position (Q1) at this time, the point B of the plate 70 is pushed upwardly to the height +hB, and the point D is moved down to the height −hD (FIG. 19(A)).

(c') When the links 80, 81 turn further 45° counterclockwise, the connection 85 moves to the position (P3), so that the point A of the plate 70 is pulled down to the height of −hA, and the point C is moved upward to the height of +hC. Since the connection 86 is at the position (Q2) at this time, the points B, D of the plate 70 are at the same height as the point O (FIG. 20(A)).

(d') When the links 80, 81 are further rotated 45° counterclockwise, the connection 85 is at the position of (P4), so that the points A, C of the plate 70 are at the same position as the point O.

Then, since the connection 86 is at the position of (Q3), the point B of the plate 70 is moved down to the height of −hB, and the point D is moved upward to the height of +hD (FIG. 21(A)).

Further, when the links 80, 81 are again rotated 45° counterclockwise, the condition is returned to the above mentioned (a') state and the (a') to (d') states are repeated.

TURNING SYSTEM II

A reference will be made to a case that the shaking plate is turned around the X- and Y-axes n times irregularly, to select the relation between h0 and hA, hB, hC, hD.

FIG. 22 is a front view of the shaking device FIG. 23 is a side view of operating according to the turning system II. the device of FIG. 22. The numeral shaking plate, 70 has a center O which is pivoted at a spatial angle relative to a pole by means of a link ball 90a. 91, push bars 91, 91 are for the plate 70, and the former is pivoted on the X-axis, and the latter is pivoted on the Y-axis via link balls 90b, 90c.

The other end of the push bar 91 is turnably connected to the end of a rack 93 and the other end of the push bar 92 is turnably connected to a rack 94. The rack 93 is moved by a pinion gear 96 rotated by a motor 95. The rack 94 is moved by a pinion gear 98 rotated by a motor 97.

A device 99 controls rotation speed and rotating direction of the motors 95, 97. By the control device, the motors 95, 97 may be driven independently or concurrently.

(a") At first, the heights hA, hB, hC, hD of the points A, B, C, D of the shaking plate 70 are at the same zero level as h0 of the point O (t1 time in FIG. 24).

When the rack 93 is advanced by driving of the motor 95, the push bar 91 pushes up the plate 70. Thereby the plate 70 starts to turn about the Y-axis, and the point A moves vertically to +hA and the point C to −hC (t1+Δt time in FIG. 24).

(b") After the point A comes to the height of +hA, and the point C to the height −hC (t2 time in FIG. 24), the rack 93 is moved back by reversing the motor 95, and the push bar 91 pulls down the plate 70, and gradually the points A, C start to move to the same height as h0 (t2+Δt time in FIG. 24). Then, the points B, D are always at the same height as h0 until t1 to t2+Δt time.

(c") After the points A, B, C, D have returned to the same height as h0 (t3 time in FIG. 24), the rack 94 is advanced by the motor 97, and the push bar 92 pushes the plate 70. Thereby the plate 70 starts to turn about the X-axis, and gradually the point B starts to move vertically to +hB, and the point D to −hD (t3+Δt time in FIG. 24).

(d″) After the point B has come to +hB, and the point D to −hD (t4 time in FIG. 24), the rack 94 is moved back by reversing the motor 97, and the push bar 92 pulls down the plate 70. Therefore the plate 70 starts to turn around the X-axis, and gradually the points B, D move vertically to the same height as h0 (t4+Δt time in FIG. 24). At this time, the points A, C are at the same height as h0 until t3 to t4 +Δt.

(e″) The points A, B, C, D return to the same height as h0, and carry out the turnings as repeating the following actuations.

At t5 time and t5+Δt time, the actuation of (c″),
at t6 time and t6+Δt time, the actuation of (d″),
at t7 time and t7+Δt time, the actuation of (a″), and
at t8 time and t8+Δt time, the actuation of (b″).

Thus, in this example, the plate 70 turns alternately vertical half-cycle movements about the X-axis and half-cycle movements about the Y-axis.

The device of FIGS. 22 and 23 may also operate according to the above mentioned turning system I.

A following reference will be made to the shaking operation:

(f′) At first the points A, B, C, B are at the same height as h0 (time t9).

When the motor 97 is reversely rotated to move back the rack 94, the point B of the plate 70 is moved toward −hB around the X-axis, and the point D toward +hD (t9+Δt time in FIG. 24).

(g″) After the point B has reached the position of −hB and the point D the position +hD (t10 time in FIG. 24), the motor 95 is actuated and the rack 93 is advanced to push up the plate 70, and the plate 70 is pulled down by the motor 97 via the push bar 92. From t10+Δt time t14 time, the plate may be turned in the same way as in turning from t4+Δt time to t8 time.

In the present embodiment, it is possible to push up or pull down the shaking plate 70 at the same time via the push bars 91, 92 by rotating the motor 95 normally or reversely.

FIG. 25 shows that the shaking plate 70 in FIG. 13 is housed within a sealed container 100, and temperature therein is controlled to be optimum to the cell cultivating condition.

A sequence of steps for cultivating the cells by means of the cultivating device shown in FIG. 2 and the rotation device of FIG. 6 is as follows:

An outer bag of the cultivation container used in this example is made of polyvinyl chloride. The sheet thickness of the container is 0.4 mm, and the capacity of the container is 4,000 ml in total, the proportion of the exterior liquid being 2,000 ml and of the air being about 2,000 ml. The inner bag 3 is made of regenerated cellulose film. The film thickness is 20 μm, the molecular weight 10,000, and the capacity of the bag 3 is 1000 ml in total, the proportion of the interior liquid being 500 ml and of the air being about 500 ml. In the present operating example, an explanation will be made in reference to the cultivation of human lymphocytes. The invention is also suitable especially for the high density cultivation of a cell line derived from the blood such as mouse hybridoma.

(I) Washing of cultivation bag

The inner bag 3 is coated with glycerine against drying. Therefore, the washing is to be made with a physiological salt solution.

As shown in FIG. 26, a communication tube 111 is connected to a bag 110 holding the physiological salt solution at one end, and connected to an inner liquid handling mouth 4 (communication mouth) at the other end. The communication tube 111 has liquid lead needles 112, 113, and a clamp 114 at a middle part. The clamp 114 is at first closed, and opened after having connected the handling mouth 4 with the bag 110, thereby to pour the physiological salt solution of about 500 ml into the bag 3.

The clamp 114 is closed, and the connection tube 111 is taken off from the bag 110, after which, two parts around the handling opening 4 are knotted to seal and unnecessary parts are cut off.

The inner bag 3 is confirmed about leaking, and the physiological salt solution is charged about 2000 ml into the outer bag 1 in the same way as said above. FIG. 27 shows that after the salt solution is supplied into the outer bag 1, a communication tube 111a connected to exterior opening or mouth 2 is sealed by knots 115, 115a. Among the exterior openings 2 (communication opening), one without a protector 2a is used first.

The culture or cultivation bag is provided on a rotary agitator shown in FIG. 6, and rotated 4 to 5 rpm for about 15 minutes.

(II) Pouring of lymphocytes suspended in media (interior liquid) and of culture media (exterior liquid)

(1) Discharge of washing liquid

The culture bag is removed from the rotary agitator, and the communication tube 111a is taken off from the exterior liquid handling opening or mouth 2, and a new communication tube (clamp is closed) is connected. The clamp of the communication tube is opened, and the washing liquid within the outer bag 1 is discharged. Thereafter, the communication tube is firmly knotted twice to seal and unnecessary tube parts are cut off.

Then, the inner bag 3 is checked about leaking, and the washing liquid within the inner bag 3 is discharged in the same way as said above, and the communication tube is sealed and unnecessary parts are cut off.

The lymphocytes suspended in medium is charged into the inner bag 3 in a following procedure.

The communication tube 111 is removed from the interior liquid handling mouth 4, and an instrument 120 for pouring the cell suspending liquid is connected as shown in FIG. 28 in a manner that a leading tube 122 is connected to a funnel 121, and a needle 123 is attached to the tube 122.

After the needle 123 is pierced into the mouth 4, the lymphocytes suspended in medium is poured into the interior bag 3 due to the force of gravity.

After pouring the lymphocytes suspended in media, the pouring instrument 120 is taken off, and an adapter 130 shown in FIG. 29 is connected, which includes a cap 132 having a rubber plug at a rear portion of a liquid lead needle 131.

The adapter 130 is connected with an instrument 140 for supplying a sterilized air as shown in FIG. 30, which includes a disposable syringe 144, a three-way stopcock 143, a disposable membrane filter 142 and a disposable needle 141, connected in this order one to another.

After piercing the disposable needle 141 into the rubber plug of an operating adapter 130, the sterilized air is supplied by piston action of a syringe 144 and switching of the three-way stopcock 143 so that the inner bag 3 is inflated. The amount of the sterilized air is not determined. After supplying the sterilized air, the instrument 140 is removed.

(3) Pouring of the exterior liquid

As shown in FIG. 31, The culture media bag 150 which has been in advance prepared, is connected with one needle 112b of the connection tube 111b of the same structure as said above, and the communication tube is removed from the exterior handling mouth 2 of the outer bag, and the other needle 113b is connected to said opening 2. After then, the clamp 114b is opened, and the exterior liquid is poured by gravity.

Then, the communication tube 111b is taken off from the mouth 2, and connected with an adapter 130 of the same structure as said above.

A sterilized filter 142 and a disposable needle 141 of the sterilized air supplying instrument 140 are exchanged with new ones and the sterilized air is supplied into the outer bag 1 in the same manner as into the inner bag 3 so as to inflate the outer bag 1. The amount of the sterilized air is not determined.

(III) Starting of cultivation

A rotary agitator as shown in FIG. 6 is installed in a thermostatic chamber set at 37° C. or an incubator, and the culture bag is set as shown in FIG. 32.

The culture bag is provided on the rotary plate 40 by loosening a screw 63a of a securing unit 60 to remove a stopper ring 63 from a pin 61, mounting a securing unit 60 in each of attaching holes 7 the pins 61, inserting the stopper ring 63 onto each of tightening the screws 63a and securing the stopper ring 63 to the pin 61. Thus, each of corners of the outer bag 1 is fixed to each of the corners of the rotary plate 40.

If the culture bag had any slack, the desired shape could not be maintained, and smooth agitation could not be made. Therefore, the culture bag should be provided in tension.

The culture bag is given tension by loosening a screw 62 of a pin 61, moving the pin 61 along the hole 40a to a proper position of the cutout 40b, and fixing the pin 61 by the screw 62. The same operation is performed with the remaining securing units to give tension over the culture bag.

When the culture bag is attached to the rotary plate 40, the rotation speed is determined, and the motor 41 is driven. Since the rotary plate 40 is rotated while being tilted with respect to the horizontal surface, the culture bag is periodically reversed at the top and the bottom, so that the interior liquid and the exterior liquid are agitated within the sealed bags. Both liquids contact each other through the membrane film of the inner bag 3 as and the media in the exterior liquid moves into the interior liquid due to diffusion phenomena.

The rotation speed of the plate 40 is generally 4 to 5 rpm. The cultivation by this device is undertaken within the thermostatic chamber or the incubator the temperature of which has been set to suit the cultivation.

The culture bag is attached to the rotary plate 40, and the latter is rotated 4 to 5 rpm for doing cultivation.

(IV) Exchange of culture media (exterior liquid)

An exchanging period is judged when the exterior liquid becomes yellow. It is convenient to divide the culture media into separate culture bags.

When the culture media are to be exchanged, the rotation of the rotary agitator is stopped and the culture bag is removed. Then, the handling opening 2 for a non-used exterior liquid is connected with a communication tube (clamp is closed) of the same structure as shown in FIG. 26, and the clamp is opened to discharge the exterior liquid by the force of gravity.

After dischaging the exterior liquid, the clamp is closed, and a culture bag which has been in advance produced is connected with another communication tube (clamp is closed), after which, the communication tube connected to the opening 2 is taken off and connected with the communication opening of the culture bag, and at the same time, the clamp is opened to charge the exterior liquid by gravity.

When the pouring of the exterior liquid has been completed, the clamp is closed, and the communication tube is taken off from the culture bag and is knotted twice and firmly sealed, and unnecessary tube parts are cut off. If the outer bag lacks in tension, the sterilized air is supplied in the same way as said above.

The culture bag is fixed to the rotary agitator, and the cultivation is again performed.

(V) Finishing of the cultivation and yielding of lymphocytes suspended in media (interior liquid)

Having completed the cultivation, the culture bag is removed from the rotary agitator, and a yield bag 170 as shown in FIG. 33 is prepared.

The yield bag 170 is connected with a leading tube 171, and a liquid lead needle 172 is provided at its end portion. The lead tube 171 is knotted moderately as shown in FIG. 33 near to the bag and a loop 173 is made in advance. The operation adaptor is taken off from the handling opening 4 for the interior liquid, and the needle 172 of the yield bag 170 is connected thereto, and the interior liquid is discharged by the force of gravity into the yield bag 170 via the leading tube 171.

The loop 173 of the tube 171 is, after the discharge, firmly knotted, and the needle 172 is removed from the handling opening 4. Another knot is made near to knot, and is sealed. Unnecessary tube parts are cut off.

The above mentioned culture bag, media bag, yield bag, communication tube, operation adapter, cell pouring instrument, and sterilized air supplying instrument are all disposable products made of plastics.

The following will refer to examples of cultivating cells by using the devices of the invention.

EXAMPLE 1

The culture liquid (RPMI 1640 500 ml) containing human lymphocytes, interleukin-2 (called as "IL-2" hereinafter) and +human AB serum (20%) was sealed into the inner bag 3 of the culture device (pore size: 24 Å). The culture liquid (RPMI 1640: 2000 ml) and the air (2000 ml) were supplied into the outer bag.

The culture instrument was fixed to the rotary plate 40 of the agitator (rotation angle: 30°), and the leading of the LAK cell (lymphokine-activated killer) was carried out in an incubator. During leading, the culture liquid was exchanged via another opening.

Changings of the activated killer of LAK cell according to the invention was compared with the conventional method (roller bottle), as shown in FIG. 34, where a vertical axis indicates % of the actvated killer and the horizontal axis indicates days of cultivation; the solid line shows the yield according to present invention and the dotted line shows the prior art.

The activated killer was increasing for 16 days in the process of the invention and of the prior art. The activated killer was measured by ATP method.

The comparison between the invention and the prior art is shown in Table 1. According to the invention, in comparison with the prior art where the culture liquid and the lymphocetyes are mixed, the used-up amount of the precious IL-2 the process of the invention is 1000μ, while that of the prior art is 2500μ. The used-up amount of the human AB serum in the process of the invention is 100 ml, while that of the prior art is 1000 ml. Thus, although the invention largely decreased the amount of culture liquid, used the yield of the activated killer was equivalent in the process of the invention and the prior art. If using the disposable products as said above, then sterilized handling could be performed easier than for the conventional techiques.

TABLE 1

Comparisons in cultivation of lymphocytes of $1.0 \times 10^{10}$

|  | Prior Art | Invention |
|---|---|---|
| rIL-2 concentration | 0.5 μ/ml | 2.0 μ/ml |
| Cell concentration during cultivation | $2.0 \times 10^6$/ml | $2.0 \times 10^7$/ml |
| Required amount of IL-2 | 2500μ | 1000μ |
| Required amount of culture media | 5.0 l | Amount in half transparent film: 0.5 l<br>Amount outside half transparent film: 6 l |
| days of cultivation | 6 days | 6 days |
| Required amount of AB serum | 1000 ml | 100 ml |
| Cultivating container | Five of roller bottles of 2, 0 capacity | One cultivating bag |
| Instrument | Bottle roller | Agitator |
| Cultivating place | Exclusive incubator | Incubator of $600 \times 600 \times 600$ mm |

EXAMPLE 2

The culture liquid (Eagle's MEM) containing the air and Raji cell and FCS were sealed in the inner bag 3 of the culture container and the culture liquid (Eagle's MEM) and the air were supplied into the outer bag 3. The culture container was fixed to the rotary plate 40, and the cultivation was done in the incubator.

The increasing curves of Raji cell according to the invention and the conventional method (flask cultivation) are shown in FIG. 35, where the vertical axis indicates concentration of cell and the lateral axis indicates days of cultivation, and the solid line relates to the invention and the dotted line to the prior art.

The present inventive method and the conventional method began the cultivations at cell concentration of 50/mm$^3$. While the prior art method reached the cell concentration of 455/mm$^3$ in four days of the cultivation and thereafter it went down, the invention continued the increasing of the cell concentration up to 2060/mm$^3$ after seven days of the cultivation.

EXAMPLE 3

The air and the culture liquid (NS-1) containing the mouse hybridoma and FCS were sealed into the inner bag 3 of the culture container, and the air and the culture liquid (NS-1) were sealed in the outer bag. The culture container was fixed to the rotary plate 40 of the agitator and the cultivation was done in the incubator. The increasing curves of the hybrimoda obtained by the invention and the prior art are shown in FIG. 36.

The conventional method reached the cell concentration of 1000/mm$^3$ in four days of cultivation, and went down thereafter, but the invention continued to increase the cell concentration up to 10,000/mm$^3$ in six cultivating days.

Further investigations were made in developments of Examples 1 to 3, and excellent results are shown in Table 2, where the data concerning the prior art cultivation in flask are shown for comparison.

TABLE 2-a

| Cultivating condition | Kind of cell Mouse Hybridoma (NS-1 Mother cell) | | | |
|---|---|---|---|---|
| Kind of cultivation | With FCS | With FCS | Completely serum-free | Completely serum-free |
| Components of interior medium | 20% FCS + NS-1 | 20% FCS + NS-1 | 2% BSA + NYSF-404 + 0.01% Trypsin | 2% BSA + NYSF-404 + 0.01% Trypsin |
| Volume of interior medium | 5 ml | 5 ml | 5 ml | 5 ml |
| Number of cells at state of cultivation | $2.0 \times 10^5$/ml | $2.0 \times 10^5$/ml | $2.0 \times 10^5$/ml | $2.0 \times 10^5$/ml |
| Components of exterior medium | NS-1 | NYSF-404 (No insulin, BSA, Transferrin) | NYSF-404 (No insulin, BSA, Transferrin) | NYSF-404 (No insulin, BSA, Transferrin) |
| Period of cultivation | 9 days | 7 days | 6 days | 6 days |
| Cell concentration at the end of cultivation ($10^7$/ml) | 1.0–1.3 | 1.3–1.6 | 1.5–2.0 | 2.0–3.0 |
| Gross volume of exterior medium | 1.0–1.2 l | 1.0–1.2 l | 1.0–1.2 l | 1.0–1.2 l |
| Comparison data: Cultivation by conventional flask methods Flask media | 20% FCS + NS-1 | 20% FCS + NS-1 | NYSF-404 (completely SERUM-FREE) | NYSF-404 (Completely SERUM-FREE) |
| Upper limit of cultivation using flask ($10^6$/ml) | 0.7–0.8 | 0.7–0.8 | 0.6–0.7 | 0.6–0.7 |
| Increased density of CR tissue cell vs flask | 14–16 x | 18–20 x | 25–28 x | 33–43 x |
| Increased density | 60–120 x | 120 x | 120 x | 120–240 x |

TABLE 2-a-continued

| Culti-vating condition | Kind of cell Mouse Hybridoma (NS-1 Mother cell) | | | |
|---|---|---|---|---|
| of monoclonal antibodies vs Standard methods | | | | |
| Cells in flask | Epith | Epith | Lym | Lym |
| Remarks | | | | *E-NYSF404 (enriched NYSF-404) |

TABLE 2-b

| Culti-vating condition | Kind of cell | | | |
|---|---|---|---|---|
| | Raji cell | Lymphocyte (Human) | | |
| Kind of cultivation | With FCS | LAK Induction | PHA Rejuvenation | PHA BLAST Cultivation |
| Components of interior medium | 20% FCS + Eagle's MEM | 5 u/m rIL-2 + 20% AB serum + RPMI 1640 | 1% PHA-H + 10% FCS + RPMI 1640 | 5 u/m rIL-2 + 10% FCS + RPMI 1640 |
| Volume of interior medium | 5 ml | 500 ml | 5 ml | 5 ml |
| Number of cells at state of cultivation | $2.0 \times 10^5$/ml | $2.0 \times 10^7$/ml | $1.0 \times 10^6$/ml | $1.0 \times 10^6$/ml |
| Components of exterior medium | Eagle's MEM | RPMI 1640 | RPMI 1640 | RPMI 1640 + 0.0032% |
| Period of cultivation | 5 days | 6 days | 7 days | 7 days |
| Cell concentration at the end of cultivation ($10^7$/ml) | 1.00–1.30 | 0.9–1.4 | 0.6–1.6 | 0.8–1.2 |
| Gross volume of exterior medium | 1.0–1.4 l | 8.0–12.0 l | 0.1–0.2 l | 0.4–0.6 l |
| Comparison data: Cultivation by conventional flask methods Flask media | 10% FCS + Eagle's MEM | 20% AB serum + 0.5 u/m rIL-2 + RPMI 1640 | 10% FCS + 1% PHA-M + RPMI 1640 | 10% FCS + 5 u/m rIL-2 + RPMI 1640 |
| Upper limit of cultivation using flask ($10^6$/ml) | 0.4–0.6 | 2.0–2.5 | 1.0–2.0 | 1.0–2.0 |
| Increased density of CR tissue cell vs flask | 25–32 x | 8–10 x | 3–10 x | 5–8 x |
| Increased density of monoclonal antibodies vs Standard methods | | | Not test | |
| Cells in flask | Lym | Lym | Lym Agricated | Lym |
| Remarks | | | | |

TABLE 2-c

| Culti-vating condition | Kind of cell HeLa | | |
|---|---|---|---|
| Kind of cultivation | With FCS | With FCS | Completely SERUM-FREE |
| Components of interior medium | 10% FCS + Eagle's MEM | 10% FCS + Eagle's MEM + 0.1% Trypsin | 2% BSA + NYSF-404 + 0.05% Trypsin |
| Volume of interior medium | 5 ml | 5 ml | 5 ml |
| Number of cells at state of cultivation | $2.0 \times 10^5$/ml | $2.0 \times 10^5$/ml | $2.0 \times 10^5$/ml |
| Components of exterior medium | Eagle's MEM | Eagle's MEM | NYSF-404 (No insulin, BSA, Transferrin |
| Period of cultivation | 5 days | 8 days | 8 days |
| Cell concentration at the end of cultivation ($10^7$/ml) | 0.2–0.4 | 0.8–1.2 | 0.6–1.0 |
| Gross volume of exterior medium | 0.8–1.0 l | 0.8–1.2 l | 0.4–0.8 l |
| Comparison data: Cultivation by conventional flask methods Flask media | 10% FCS + Eagle's MEM | 10% FCS + Eagle's MEM | NYSF-404 (Completely SERUM-FREE |
| Upper limit of cultivation using flask ($10^6$/ml) | 0.2–0.4 | 0.2–0.4 | 0.2–0.4 |
| Increased density of CR tissue cell vs flask | 10–20 x | 30–40 x | 25–30 x |
| Increased density of monoclonal antibodies vs Standard methods | | | |
| Cells in flask | Epith | Epith | Epith |

TABLE 2-c-continued

| Culti-vating condition | Kind of cell HeLa |
|---|---|
| Remarks | |

TABLE 2-d

| Culti-vating condition | Kind of cell | | |
|---|---|---|---|
| | MDT-4 | SU-1 | HBS |
| Kind of cultivation | With FCS | With FCS | With FCS |
| Components of interior medium | 20% FCS + RPMI 1640 | 20% FCS + McCoy's 5A | 20% FCS + RPMI 1640 |
| Volume of interior medium | 5 ml | 5 ml | 5 ml |
| Number of cells at state of cultivation | $2.0 \times 10^5$/ml | $4.0 \times 10^5$/ml | $3.0 \times 10^5$/ml |
| Components of exterior medium | RPMI 1640 | McCoy's 5A | RPMI 1640 |
| Period of cultivation | 9 days | 4 days | 7 days |
| Cell concentration at the end of cultivation ($10^7$/ml) | 1.2–1.4 | 1.0–1.2 | 1.4–1.6 |
| Gross volume of exterior medium | 0.8–1.2 l | 0.4–0.8 l | 0.8–1.0 l |
| Comparison data: Cultivation by conventional flask methods Flask media | 10% FCS + RPMI 1640 | 10% FCS + McCoy's 5A | 10% FCS + RPMI 1640 |
| Upper limit of cultivation using flask ($10^6$/ml) | 1.0–1.2 | 0.3–0.5 | 1.0–1.2 |
| Increased density of CR tissue cell vs flask | 12–13 x | 24–33 x | 13–14 x |
| Increased density of monoclonal antibodies vs Standard methods Cells in flask | Lymp | Lymp | Lymp |
| Remarks | | *SU-1 Derived from Ovarian Carcinoma | |

CR Tissue: Notes
(1) FCS = Fetal Calf Serum
(2) PHA = Phytohemaglutinin Rejuvenation
(3) BSA = Bovine Serum Albumin
(4) Epith = Epithelial-like cell
(5) Lymph = Lymphoblast-like cell
(6) E-NYSF-404 = Enriched NYSF-404
(7) SU-1 = Derived from Ovarian Carcinoma As mentioned above, according to the present invention, the following excellent effects could be brought about:

(1) In comparison with the prior art, effective and economical cultivation is possible. Actually, for example (Example 1), the amount used of IL-2 and of the human AB serum may be largely decreased, and in cell cultivations in Examples 2 and 3 and Table 2, a substantially higher concentration is obtained in comparison with the prior art. It is possible to culture the cells by changing, if necessary, the media in the semipermeable membrane film container and the components of the media outside of the membrane film container.

(2) The cultivation within the sealed bag is possible, and since the media liquid is not circulated as is done in the conventional hollow membrane, the sterilized operation may be easily made.

(3) The cultivation is possible within narrow spaces and with small size instruments in contrast to the rotary cultivation by the conventional roller bottle. Further, as in the cultivation with the hollow membrane, no complicated system is required, and much condensed cultivation is made possible.

(4) The cells to be cultivated and the culture media are sealed in different containers. The charging and yielding of the cells, the exchanging of the culture media, and the supplying of the sterilized air are carried out by an easy one touch connection of the operating instrument.

(5) By using each of the above mentioned instruments, the cell yielding and exchange of the culture media may be carried out under the sterilized condition.

(6) In comparison with the rotary cultivation by the conventional roller bottle, nutrition passes to the cells through the semipermeable film, and by exchanging the culture media it is possible to cultivate the cells in the semipermeable film container at high concentration.

(7) Since the cells and the culture media are moderately agitated, the component of the cell is uniformly dispersed, and the cells do not attach to the wall of the container or cause condensation, and the high yield may be obtained. In addition, the cultivation is carried out while rotating or shaking the culture container, so that much cultivation is possible in spite of the small area of the film in comparison to the conventional culture container of the hollow membrane.

What is claimed is:

1. A method for culturing tissue cells, comprising the steps of:
    (a) suspending the cells to be cultured in an amount of culture liquid;
    (b) enclosing and sealing the culture liquid with the cells to be cultured in an inner container comprising a semipermeable membrane film;
    (c) positioning the inner container in a soft plastic outer container with a protective plastic mesh surrounding said inner container so as to prevent said inner container from contacting said outer container;
    (d) retaining another amount of culture liquid and gas in the outer container in contact with the semipermeable membrane film of the inner container;
    (e) sealing the outer container;
    (f) culturing the cells within the inner container by diffusing a portion of the culture liquid and gas from the outer container through the semipermeable membrane film into the inner container, the diffusing taking place due to a difference in concentration between the culture liquid inside and outside of the inner container and shaking the two containers on a shaking plate during culturing of the cells to enhance the diffusing, said shaking plate having a center point where a first axis and a second axis intersect perpendicular to one another, said shaking including oscillating said shaking plate alternatively about said first axis and said second axis for a predetermined length of time;
    (g) after said predetermined length of time, unsealing the outer container and replacing said another amount of culture liquid and gas in the outer container with a new fresh amount of culture liquid and gas and again sealing the outer container; and
    (h) repeating steps (f) and (g) until said culturing is finished.

2. A method as defined in claim 1, wherein the tissue cells to be cultivated are selected from the group consisting of human lymphocyte cells, mouse hybridoma cells and other blood cells.

3. A method of culturing animal tissue cells in an assembly of an inner container of semipermeable membrane film, a soft plastic outer container housing the inner container, and a protective plastic mesh surrounding said inner container so as to prevent said inner container from contacting said outer container, the method comprising the steps of:

rinsing the inner container with a rinsing liquid, introducing a first amount of culture liquid together with cells to be cultured into the inner container and introducing a sterilized air into the inner container and sealing the inner container, said cells being selected from the group consisting of human lymphocyte cells, mouse hybridoma cells and other blood cells;

introducing a second amount of culture liquid and sterilized air into the outer container and sealing the outer container, inclining said inner and outer containers from about 30° to 60°;

imparting a rotary movement to the containers, said rotary movement being at a rate of 0.5 to 10 rpm, so that, during culturing of the cells, culture media contained in the second amount of culture liquid are transferred by diffusion phenomena into the first amount of culture liquid; and halting the imparting of the rotary movement, unsealing the outer container, replacing the second amount of culture liquid in the outer container with a fresh amount of culture liquid and sterilized air and again sealing the outer container.

4. A method as defined in claim 3, wherein the culture liquid supported in the inner container contains at least one breeding factor of the animal tissue cells to be cultivated and at least one serum, while the culture liquid in the outer container contains at least one serum.

5. A method as defined in claim 3, wherein the semipermeable film has a plurality of pores and each of the pores has a diameter not exceeding 0.2 micrometers.

* * * * *